US012139731B2

(12) United States Patent
Wiedenheft et al.

(10) Patent No.: US 12,139,731 B2
(45) Date of Patent: Nov. 12, 2024

(54) CRISPR-BASED PROGRAMMABLE RNA EDITING

(71) Applicant: Montana State University, Bozeman, MT (US)

(72) Inventors: Blake A. Wiedenheft, Bozeman, MT (US); Joseph E. Nichols, Bozeman, MT (US); Anna A. Nemudraia, Bozeman, MT (US); Artem A. Nemudryi, Bozeman, MT (US)

(73) Assignee: NATIONAL INSTITUTES OF HEALTH (NIH), U.S. DEPT. OF HEALTH AND HUMAN SERVICES (DHHS) U.S. GOVERNMENT, Bethesda, MD (US)

( * ) Notice: Subject to any disclaimer, the term of this patent is extended or adjusted under 35 U.S.C. 154(b) by 0 days.

(21) Appl. No.: 17/811,391

(22) Filed: Jul. 8, 2022

(65) Prior Publication Data

US 2023/0040061 A1 Feb. 9, 2023

Related U.S. Application Data

(60) Provisional application No. 63/219,722, filed on Jul. 8, 2021.

(51) Int. Cl.

| | |
|---|---|
| *C12N 9/22* | (2006.01) |
| *C12N 7/00* | (2006.01) |
| *C12N 15/11* | (2006.01) |
| *C12N 15/66* | (2006.01) |

(52) U.S. Cl.

CPC ................ *C12N 9/22* (2013.01); *C12N 7/00* (2013.01); *C12N 15/11* (2013.01); *C12N 15/66* (2013.01); *C12N 2310/20* (2017.05); *C12N 2770/20021* (2013.01); *C12N 2770/20052* (2013.01); *C12N 2800/80* (2013.01)

(58) Field of Classification Search
None
See application file for complete search history.

(56) References Cited

U.S. PATENT DOCUMENTS

| | | | |
|---|---|---|---|
| 9,115,348 | B2 | 8/2015 | Haurwitz et al. |
| 9,688,971 | B2 | 6/2017 | Doudna et al. |
| 10,253,365 | B1 | 4/2019 | Doudna et al. |
| 10,266,886 | B2 | 4/2019 | Abudayyeh et al. |
| 10,337,051 | B2 | 7/2019 | Doudna et al. |
| 10,494,620 | B2 | 12/2019 | Doudna et al. |
| 10,494,664 | B2 | 12/2019 | Doudna et al. |
| 10,648,020 | B2 | 5/2020 | Zhang et al. |
| 10,844,378 | B2 | 11/2020 | Siksnys et al. |
| 11,001,829 | B2 | 5/2021 | Zhang et al. |
| 11,021,740 | B2 | 6/2021 | Abudayyeh et al. |
| 11,104,937 | B2 | 8/2021 | Abudayyeh |
| 11,118,224 | B2 | 9/2021 | Doudna et al. |
| 11,174,515 | B2 | 11/2021 | Abudayyeh et al. |
| 11,180,792 | B2 | 11/2021 | O'Connell et al. |
| 11,299,732 | B2 | 4/2022 | Marraffini et al. |
| 11,814,689 | B2 * | 11/2023 | Wiedenheft ........... C12Q 1/701 |
| 2014/0186843 | A1 | 7/2014 | Zhang et al. |
| 2016/0017396 | A1 | 1/2016 | Cann et al. |
| 2016/0068822 | A1 | 3/2016 | Zhang et al. |
| 2016/0317677 | A1 | 11/2016 | Bhatia et al. |
| 2018/0112255 | A1 | 4/2018 | Chen et al. |
| 2018/0142222 | A1 | 5/2018 | Sternberg et al. |
| 2018/0208976 | A1 | 7/2018 | Doudna et al. |
| 2018/0251787 | A1 | 9/2018 | Hatoum |
| 2018/0305773 | A1 | 10/2018 | Abudayyeh et al. |
| 2019/0161753 | A1 | 5/2019 | Terns et al. |
| 2019/0177775 | A1 | 6/2019 | Doudna et al. |
| 2019/0241954 | A1 | 8/2019 | Doudna et al. |
| 2019/0256900 | A1 | 8/2019 | Zhang et al. |

(Continued)

FOREIGN PATENT DOCUMENTS

| | | | |
|---|---|---|---|
| CN | 110982945 | A | 4/2020 |
| CN | 111996236 | A | 11/2020 |

(Continued)

OTHER PUBLICATIONS

Lau et al., "Attenuated SARS-COV-2 variants with deletions at the S1/S2 junction" 9 Emerging Microbes & Infections 837-842 (Year: 2020).*
Santiago-Frangos et al., "Intrinsic signal amplification by type III CRISPR-Cas systems provides a sequence-specific SARS-CoV-2 diagnostic" 2 Cell Reports Medicine 1-8, e1-e5 (Year: 2021).*
Moore et al., "Joining of RNAs by Splinted Ligation" 317 Methods in Enzymology 109-123 (Year: 2000).*
Athukoralage et al., "The dynamic interplay of host and viral enzymes in type III CRISPR-mediated cyclic nucleotide signalling", eLife Research Advance, 2020, pp. 1-16, vol. 9:e55852.

(Continued)

*Primary Examiner* — Nancy J Leith
(74) *Attorney, Agent, or Firm* — Pillsbury Winthrop Shaw Pittman LLP

(57) ABSTRACT

CRISPR RNA-guided nucleases are routinely used for sequence-specific manipulation of DNA. While CRISPR-based DNA editing has become routine, analogous methods for editing RNA have yet to be established. Here we repurpose the type III-A CRISPR RNA-guided nuclease for sequence-specific cleavage of the SARS-CoV-2 genome. The type III cleavage reaction is performed in vitro using purified viral RNA, resulting in sequence-specific excision of 6, 12, 18 or 24 nucleotides. Ligation of the cleavage products is facilitated by a DNA splint that bridges the excision and RNA ligase is used to link the RNA products before transfection into mammalian cells. The SARS-CoV-2 RNA is infectious and standard plaque assays are used to recover viral clones. Collectively, this work demonstrates how type III CRISPR systems can be repurposed for sequence-specific editing of RNA viruses including SARS-CoV-2 and more generally for gene therapy.

15 Claims, 7 Drawing Sheets

Specification includes a Sequence Listing.

(56) References Cited

U.S. PATENT DOCUMENTS

| | | |
|---|---|---|
| 2019/0300908 A1 | 10/2019 | Doudna et al. |
| 2019/0359971 A1 | 11/2019 | Zhang et al. |
| 2019/0382800 A1 | 12/2019 | Severinov et al. |
| 2020/0010878 A1 | 1/2020 | Doudna et al. |
| 2020/0032324 A1 | 1/2020 | Baughman et al. |
| 2020/0080137 A1 | 3/2020 | Green et al. |
| 2020/0087642 A1 | 3/2020 | Doudna et al. |
| 2020/0165594 A1 | 5/2020 | Zhang et al. |
| 2020/0181720 A1 | 6/2020 | Omar et al. |
| 2020/0231975 A1 | 7/2020 | Gootenberg et al. |
| 2020/0248229 A1 | 8/2020 | Zhang et al. |
| 2020/0254443 A1 | 8/2020 | Zhang et al. |
| 2020/0263166 A1 | 8/2020 | Zhang et al. |
| 2020/0277600 A1 | 9/2020 | Zhang et al. |
| 2020/0332272 A1 | 10/2020 | Zhang et al. |
| 2020/0370028 A1 | 11/2020 | Doudna et al. |
| 2020/0392473 A1 | 12/2020 | Zhang et al. |
| 2020/0399697 A1 | 12/2020 | Doudna et al. |
| 2021/0017508 A1 | 1/2021 | Doudna et al. |
| 2021/0071158 A1 | 3/2021 | Zhang et al. |
| 2021/0102197 A1 | 4/2021 | Sabeti et al. |
| 2021/0102242 A1 | 4/2021 | Chen et al. |
| 2021/0108267 A1 | 4/2021 | Zhang et al. |
| 2021/0130799 A1 | 5/2021 | Siksnys et al. |
| 2021/0147915 A1 | 5/2021 | Zhang et al. |
| 2021/0163944 A1 | 6/2021 | Zhang et al. |
| 2021/0164025 A1 | 6/2021 | Blake et al. |
| 2021/0172017 A1 | 6/2021 | Jin et al. |
| 2021/0214697 A1 | 7/2021 | Doudna et al. |
| 2021/0269858 A1 | 9/2021 | Chiu et al. |
| 2021/0269866 A1 | 9/2021 | Zhang et al. |
| 2021/0292721 A1 | 9/2021 | Zhang et al. |
| 2021/0292823 A1 | 9/2021 | Zhang et al. |
| 2021/0292824 A1 | 9/2021 | Zhang et al. |
| 2021/0309981 A1 | 10/2021 | Doudna et al. |
| 2021/0317527 A1 | 10/2021 | Doudna et al. |
| 2021/0332446 A1 | 10/2021 | Wiedenheft et al. |
| 2021/0348212 A1 | 11/2021 | Fozouni et al. |
| 2021/0348243 A1 | 11/2021 | Ott et al. |
| 2021/0355487 A1 | 11/2021 | Doudna et al. |
| 2021/0371926 A1 | 12/2021 | Zhang et al. |
| 2021/0388437 A1 | 12/2021 | Doudna et al. |
| 2022/0025463 A1 | 1/2022 | Abudayyeh et al. |

FOREIGN PATENT DOCUMENTS

| | | |
|---|---|---|
| WO | 2011/143124 A2 | 11/2011 |
| WO | 2013/082519 A2 | 6/2013 |
| WO | 2013/188638 A2 | 12/2013 |
| WO | 2014/093709 A1 | 6/2014 |
| WO | 2014/145599 A2 | 9/2014 |
| WO | 2014/204727 A1 | 12/2014 |
| WO | 2015/089277 A1 | 6/2015 |
| WO | 2016/049258 A2 | 3/2016 |
| WO | 2016/094872 A1 | 6/2016 |
| WO | 2016/100974 A1 | 6/2016 |
| WO | 2016/108926 A1 | 7/2016 |
| WO | 2016/123243 A1 | 8/2016 |
| WO | 2017/205668 A1 | 11/2017 |
| WO | 2017/219027 A1 | 12/2017 |
| WO | 2018/035388 A1 | 2/2018 |
| WO | 2018/107129 A1 | 6/2018 |
| WO | 2018/170340 A1 | 9/2018 |
| WO | 2018/191388 A1 | 10/2018 |
| WO | 2019/010422 A1 | 1/2019 |
| WO | 2019/051318 A1 | 3/2019 |
| WO | 2019/071051 A1 | 4/2019 |
| WO | 2019/089808 A1 | 5/2019 |
| WO | 2019/089820 A1 | 5/2019 |
| WO | 2019/104058 A1 | 5/2019 |
| WO | 2019/126577 A2 | 6/2019 |
| WO | 2019/148206 A1 | 8/2019 |
| WO | 2019237032 | 12/2019 |
| WO | 2020/006036 A1 | 1/2020 |
| WO | 2020/006049 A1 | 1/2020 |
| WO | 2020/006067 A1 | 1/2020 |
| WO | 2020/028180 A1 | 2/2020 |
| WO | 2020/028729 A1 | 2/2020 |
| WO | 2020/041456 A1 | 2/2020 |
| WO | 2020/046809 A1 | 3/2020 |
| WO | 2020/051452 A2 | 3/2020 |
| WO | 2020/092553 A1 | 5/2020 |
| WO | 2020/092725 A1 | 5/2020 |
| WO | 2020/106630 A1 | 5/2020 |
| WO | 2020/169970 A1 | 5/2020 |
| WO | 2020/142739 A1 | 7/2020 |
| WO | 2020/142754 A2 | 7/2020 |
| WO | 2020/181101 A1 | 9/2020 |
| WO | 2020/186231 A2 | 9/2020 |
| WO | 2020/223634 A1 | 11/2020 |
| WO | 2020/256553 A1 | 12/2020 |
| WO | 2020/257356 A2 | 12/2020 |
| WO | 2021/016453 A1 | 1/2021 |
| WO | 2021/021532 A1 | 2/2021 |
| WO | 2021/026227 A1 | 2/2021 |
| WO | 2021/046257 A1 | 3/2021 |
| WO | 2021/055874 A1 | 3/2021 |
| WO | 2021/087203 A1 | 5/2021 |
| WO | 2021/133829 A1 | 7/2021 |
| WO | 2021133977 | 7/2021 |
| WO | 2021/159020 A2 | 8/2021 |
| WO | 2021/163584 A1 | 8/2021 |
| WO | 2021/188830 A2 | 9/2021 |
| WO | 2021/207702 A1 | 10/2021 |
| WO | 2021/216772 A1 | 10/2021 |
| WO | 2021/216868 A1 | 10/2021 |
| WO | 2021/236850 A1 | 11/2021 |
| WO | 2021/243308 A2 | 12/2021 |
| WO | 2022/006536 A1 | 1/2022 |

OTHER PUBLICATIONS

Broughton et al., "CRISPR-Cas12-based detection of SARS-CoV-2", Nature Biotechnology, Jul. 2020, pp. 870-874, vol. 38.

Chen et al., "CRISPR-Cas12a target binding unleashes indiscriminate single-stranded DNase activity", Science, Apr. 27, 2018, pp. 436-439, vol. 360.

Dao Thi et al., "A colorimetric RT-LAMP assay and LAMP-sequencing for detecting SARS-CoV-2 RNA in clinical samples", Science Translational Medicine, Aug. 12, 2020, pp. 1-13, vol. 12, eabc7075.

Elbe et al., "Data, disease and diplomacy: GISAID's innovative contribution to global health", Global Challenges, Jan. 10, 2017, pp. 33-46, vol. 1(1).

Elmore et al., "Bipartite recognition of target RNAs activates DNA cleavage by the Type III-B CRISPR-Cas system", Genes & Development, Feb. 15, 2016, pp. 447-459, vol. 30(4).

Fozouni et al., "Amplification-free detection of SARS-CoV-2 with CRISPR-Cas13a and mobile phone microscopy", Cell, Jan. 21, 2021, pp. 323-333, vol. 184.

Gootenberg et al., "Nucleic acid detection with CRISPR-Cas13a/C2c2", Science, Apr. 28, 2017, pp. 438-442, vol. 356.

Gootenberg et al., "Multiplexed and portable nucleic acid detection platform with Cas13, Cas12a, and Csm6", Science, Apr. 27, 2018, pp. 439-444, vol. 360.

Grubaugh et al., "An amplicon-based sequencing framework for accurately measuring intrahost virus diversity using PrimalSeq and iVar", Genome Biology, 2019, pp. 1-19, vol. 20(8).

Hale et al., "RNA-Guided RNA Cleavage by a CRISPR RNA-Cas Protein Complex", Cell, Nov. 25, 2009, pp. 945-956, vol. 139.

Zhang, Jing et al., "Multiple nucleic acid cleavage modes in divergent type III CRISPR systems", Nucleic Acids Research, Jan. 21, 2016, pp. 1789-1799, vol. 44(4).

Joung et al., "Detection of SARS-CoV-2 with SHERLOCK One-Pot Testing", The New England Journal of Medicine, Sep. 16, 2020, pp. 1492-1495, vol. 353.

Katoh et al., "MAFFT Multiple Sequence Alignment Software Version 7: Improvements in Performance and Usability", Mol. Biol. Evol., Jan. 16, 2013, pp. 772-780, vol. 30(4).

Kazlauskiene et al., "Spatiotemporal Control of Type III-A CRISPR-Cas Immunity: Coupling DNA Degradation with the Target RNA Recognition", Molecular Cell, Apr. 21, 2016, pp. 296-306, vol. 62.

(56) References Cited

OTHER PUBLICATIONS

Kazlauskiene et al., "A cyclic oligonucleotide signaling pathway in type III CRISPR-Cas systems", Science, Aug. 11, 2017, pp. 605-609, vol. 357.
Larremore et al., "Test sensitivity is secondary to frequency and turnaround time for COVID-19 screening", Science Advances, Jan. 1, 2021, pp. 1-10, vol. 7.
Lascola et al., "Viral RNA load as determined by cell culture as a management tool for discharge of SARS-CoV-2 patients from infectious disease wards", European Journal of Clinical Microbiology & Infectious Diseases, 2020, pp. 1059-1061, vol. 39.
Lazer et al., "The State of the Nation: a 50-State COVID-19 Survey Report #8: Failing the Test: Waiting Times for Covid Diagnostic Tests Across the U.S.", The COVID-19 Consortium for Understanding the Public's Policy Preferences Across States, Aug. 3, 2020, pp. 1-7.
Liu et al., "Target preference of Type III-A CRISPR-Cas complexes at the transcription bubble", Nature Communications, 2019, pp. 1-13.
Liu et al., "RNA and DNA Targeting by a Reconstituted Thermus thermophilus Type III-A CRISPR-Cas System", PLOS One, Jan. 23, 2017, pp. 1-20.
Makarova et al., "Evolutionary and functional classification of the CARF domain superfamily, key sensors in prokaryotic antivirus defense", Nucleic Acids Research, Jul. 31, 2020, pp. 8828-8847, vol. 48(16).
Nasef et al., "Regulation of cyclic oligoadenylate synthesis by the *Staphylococcus epidermidis* Cas 10-Csm complex", RNA, 2019, pp. 948-962, vol. 25(8).
Nemudryi et al., "SARS-COV-2 genomic surveillance identifies naturally occurring truncations of ORF7a that limit immune suppression", medRxiv preprint, Mar. 10, 2021, pp. 1-11.
Niewoehner et al., "Type III CRISPR-Cas systems produce cyclic oligoadenylate second messengers", Nature, Jul. 19, 2017, pp. 543-548.
Notomi et al., "Loop-mediated isothermal amplification of DNA", Nucleic Acids Research, 2000, pp. 1-7, vol. 28(12), 63.
Paltiel et al., "Assessment of SARS-CoV-2 Screening Strategies to Permit the Safe Reopening of College Campuses in the United States", JAMA Network Open, Jul. 31, 2020, pp. 1-12, vol. 3(7):e2016818.
Rambaut et al., "A dynamic nomenclature proposal for SARS-CoV-2 lineages to assist genomic epidemiology", Nature Microbiology, Nov. 2020, pp. 1403-0407, vol. 5.
Rolando et al., "Real-time kinetics and high-resolution melt curves in single-molecule digital LAMP to differentiate and study specific and non-specific amplification", Nucleic Acids Research, Feb. 27, 2020, pp. 1-21, vol. 48(7), e42.
Rouillon et al., "Control of cyclic oligoadenylate synthesis in a type III CRISPR system", eLife, Jul. 2, 2018, pp. 1-22, vol. 7, e36734.
Samai et al., "Co-transcriptional DNA and RNA Cleavage during Type III CRISPR-Cas Immunity", Cell Press, May 21, 2015, pp. 1164-1174, vol. 161.
Sofos et al., "Structures of the Cmr-b Complex Reveal the Regulation of the Immunity Mechanism of Type III-B CRISPR-Cas", Molecular Cell, Sep. 3, 2020, pp. 741-757, vol. 79.
Staals et al., "RNA Targeting by the Type III-A CRISPR-Cas Csm Complex of Thermus thermophilus", Molecular Cell, Nov. 20, 2014, pp. 518-530, vol. 56.
Tamulaitis et al., "Programmable RNA Shredding by the Type III-A CRISPR-Cas System of *Streptococcus thermophilus*", Molecular Cell, Nov. 20, 2014, pp. 506-517, vol. 56.
Tomita et al., "Loop-mediated isothermal amplification (LAMP) of gene sequences and simple visual detection of products", Nature Protocols, Apr. 24, 2008, pp. 877-882, vol. 3(5).
Tyson et al., "Improvements to the ARTIC multiplex PCR method for SARS-COV-2 genome sequencing using nanopore", bioRxiv, Sep. 4, 2020, pp. 1-19.
Wolfel et al., "Virological assessment of hospitalized patients with COVID-2019", Nature, May 28, 2020, pp. 465-469, vol. 581.

Yan et al., "Functionally diverse type V CRISPR-Cas systems", Science, Jan. 4, 2019, pp. 88-91, vol. 363.
Zhang, Yinhua et al., "Enhancing colorimetric loop-mediated isothermal amplification speed and sensitivity with guanidine chloride", BioTechniques, Jul. 8, 2020, pp. 179-185, vol. 69.
Abudayyeh et al., "New CRISPR enzyme activities add to the nucleic acid detection arsenal", Science, May 28, 2021, pp. 914-915, vol. 372 (6545).
Allan-Blitz et al.,"A Real-World Comparison of SARS-CoV-2 Rapid Antigen Testing versus PCR Testing in Florida", Journal of Clinical Microbiology, Oct. 2021, vol. 59(10).
Athukoralage et al.,"A Type III CRISPR Ancillary Ribonuclease Degrades Its Cyclic Oligoadenylate Activator", Journal of Molecular Biology, Jul. 12, 2019, pp. 2894-2899, vol. 431(15).
Athukoralage et al.,"Ring nucleases deactivate type III CRISPR ribonucleases by degrading cyclic bligoadenylate", Nature, Oct. 11, 2018, pp. 277-280, vol. 562(7726).
Bailey et al., "Fitting a mixture model by expectation maximization to discover motifs in biopolymers", Proceedings International Conference on Intelligent Systems for Molecular Biology, 1994, pp. 28-36.
Batejat et al., "Heat inactivation of the severe acute respiratory syndrome coronavirus 2", Journal of Biosafety and Biosecurity, 2021, pp. 1-3, vol. 3.
Capella-Gutierrez et al., "trimAl: a tool for automated alignment trimming in large-scale phylogenetic analyses", Bioinformatics, Jun. 8, 2009, pp. 1972-1973, vol. 25(15).
Darriba et al., "ProtTest 3: fast selection of best-fit models of protein evolution", Bioinformatics, Feb. 17, 2011, pp. 1164-1165, vol. 27(8).
Drain et al., "Rapid Diagnostic Testing for SARS-CoV-2", The New England Journal of Medicine, Jan. 7, 2022, pp. 264-272, vol. 386.
Finn et al., "HMMER web server: interactive sequence similarity searching", Nucleic Acids Research, May 18, 2011, pp. W29-W37, vol. 39.
Foster et al., "Regulation of the RNA and DNA nuclease activities required for Pyrococcus furiosus Type III-B CRISPR-Cas immunity", Nucleic Acids Research, Mar. 21, 2020, pp. 4418-4434, vol. 48(8).
Garcia-Doval et al., "Activation and self-inactivation mechanisms of the cyclic oligoadenylate-dependent CRISPR ribonuclease Csm6", Nature Communications, 2020, pp. 1-9, vol. 11(1596).
Gouveia-Oliveira et al., "MaxAlign: maximizing usable data in an alignment", BMC Bioinformatics, Aug. 28, 2007, pp. 1-8, vol. 8(312.
Gruschow et al., "Specificity and sensitivity of an RNA targeting type III CRISPR complex coupled with a NucC endonuclease effector", Nucleic Acids Research, Dec. 6, 2021, pp. 13122-13134, vol. 49(22).
Jain et al., "Nanopore sequencing and assembly of a human genome with ultra-long reads", Nature Biotechnology, Jan. 29, 2018, pp. 338-353, vol. 36(4).
Jia et al., "CRISPR-Cas III-A Csm6 CARF Domain Is a Ring Nuclease Triggering Stepwise cA4 Cleavage with ApA>p Formation Terminating RNase Activity", Molecular Cell, Sep. 5, 2019, pp. 944-956, vol. 75.
Jiang et al., "Degradation of Phage Transcripts by CRISPRAssociated RNases Enables Type III CRISPR-Cas Immunity", Cell, Feb. 11, 2016, pp. 710-721, vol. 164.
Jiao et al., "Noncanonical crRNAs derived from host transcripts enable multiplexable RNA detection by Cas9", Science, May 28, 2021, pp. 941-948, vol. 372.
Kaminski et al., "CRISPR-based diagnostics", Nature Biomedical Engineering, Jul. 2021, pp. 643-656, vol. 5.
Lau et al., "Structure and Mechanism of a Cyclic Trinucleotide-Activated Bacterial Endonuclease Mediating Bacteriophage Immunity", Molecular Cell, Feb. 20, 2020, pp. 723-733, vol. 77.
Lee et al., "CRISPR-Cap: multiplexed double-stranded DNA enrichment based on the CRISPR system", Nucleic Acids Research, Sep. 12, 2018, pp. 1-13, vol. 47(1).
Li et al., "Cd-hit: a fast program for clustering and comparing large sets of protein or nucleotide sequences", Bioinformatics, May 26, 2006, pp. 1658-1659, vol. 22(13).

(56) References Cited

OTHER PUBLICATIONS

Liu et al., "The Molecular Architecture for RNA-Guided RNA Cleavage by Cas13a", Cell, Aug. 10, 2017, pp. 714-726, vol. 170.

Liu et al., "Accelerated RNA detection using tandem CRISPR nucleases", Nature Chemical Biology, Sep. 2021, pp. 982-988, vol. 17(982).

Lowey et al., "CBASS Immunity Uses CARF-Related Effectors to Sense 30-50- and 20-50-Linked Cyclic Oligonucleotide Signals and Protect Bacteria from Phage Infection", Cell, Jul. 9, 2020, pp. 38-49, vol. 182.

Mcmahon et al., "Structure and mechanism of a Type III CRISPR defence DNA nuclease activated by cyclic oligoadenylate", Nature Communications, Jan. 24, 2020, pp. 1-11, vol. 11(1):500.

Minh el al., "IQ-TREE 2: New Models and Efficient Methods for Phylogenetic Inference in the Genomic Era", Molecular Biology and Evolution, Feb. 3, 2020, pp. 1530-1534, vol. 37(5).

Molina et al., "Structure of Csx1-cOA4 complex reveals the basis of RNA decay in Type III-B CRISPR-Cas", Nature Communications, Sep. 20, 2019, pp. 1-14, vol. 10(1):430.

Oconnell et al., "Programmable RNA recognition and cleavage by CRISPR/Cas9", Molecular Cell, Feb. 15, 2018, pp. 906-914, vol. 69(5).

Pardee et al., "Rapid, Low-Cost Detection of Zika Virus Using Programmable Biomolecular Components", Cell, May 19, 2016, pp. 1255-1266, vol. 165.

Price et al., "FastTree 2—Approximately Maximum-Likelihood Trees for Large Alignments", PLoS One, Mar. 2010, pp. 1-10, vol. 5(3).

Prince-Guerra et al., "Evaluation of Abbott BinaxNOW Rapid Antigen Test for SARS-CoV-2 Infection at Two Community-Based Testing Sites—Pima County, Arizona, Nov. 3-17, 2020", Morbidity and Mortality Weekly Report, Jan. 19, 2021, pp. 100-105, vol. 70(3).

Rostol et al., "The Card1 nuclease provides defence during type III CRISPR immunity", Nature, Feb. 25, 2021, pp. 624-649, vol. 590.

Rostol et al., "Non-specific degradation of transcripts promotes plasmid clearance during type III-A CRISPR-Cas Immunity", Nature Microbiology, Apr. 2019, pp. 656-662, vol. 4.

Schultzhause et al., "CRISPR-based enrichment strategies for targeted sequencing", Biotechnology Advances, Nov. 28, 2020, pp. 1-15, vol. 46(107672).

Smalakyte et al., "Type III-A CRISPR-associated protein Csm6 degrades cyclic hexa-adenylate activator using both CARF and HEPN domains", Nucleic Acids Research, 2020, pp. 9204-9217, vol. 45(16).

Sridhara et al., "Virus detection via programmable Type III-A CRISPR-Cas systems", Nature Communications, 2021, pp. 1-10, vol. 12(5653).

Steens et al., "SCOPE enables type III CRISPR-Cas diagnostics using flexible targeting and stringent CARF ribonuclease activation", Nature Communications, 2021, pp. 1-12, vol. 12(5033).

Ye et al., "HORMA Domain Proteins and a Trip13-like ATPase Regulate Bacterial cGAS-like Enzymes to Mediate Bacteriophage Immunity", Molecular Cell, Feb. 20, 2020, pp. 709-722.

Yu et al., "Two Methods for Mapping and Visualizing Associated Data on Phylogeny Using Ggtree", Mol. Biol. Evol., Oct. 23, 2018, pp. 3041-3043, vol. 35(12).

Zhu et al., "The CRISPR ancillary effector Can2 is a dual-specificity nuclease potentiating type Iii CRSIPR defence", Nucleic Acids Research, Feb. 15, 2021, pp. 2777-2789, vol. 49(5.).

Patent Cooperation Treaty, Preliminary Report on Patentability issued in PCT/US2021/029219, Nov. 10, 2022, pp. 1-15.

East-Seletsky, A et al., Two Distinct RNase Activities of CRISPR-C2c2 Enable Guide RNA Processing and RNA Detection, Nature, Oct. 2016.

International Search Report and Written Opinion issued in corresponding International Application No. PCT/US2022/73538, dated Oct. 27, 2022.

Sarari F. et al., CRISPR systems: Novel approaches for detection and combating COVID-19, Jan. 8, 2021, p. 7, col. 2, paragraph 2, vol. 294.

Jia et al., "Second Messenger cA4 Formation within the Composite Csm1 Palm Pocket of Type III-A CRISPRCas Csm Complex and Its Release Path", Molecular Cell, Sep. 5, 2019, pp. 933-943, vol. 75.

Wang, "One-pot Detection of COVID-19 with Real-time Reverse-transcription Loop-mediated Isothermal Amplification (RT-LAMP) Assay and Visual RT-LAMP Assay," at bioRxiv, Apr. 22, 2020, pp. 1-7.

Tucker et al., "Colorimetric Determination of pH," Journal of Chemical Education, 1989, pp. 1-3, vol. 66(9).

Abbott et al., "Development of CRISPR as a Prophylactic Strategy To Combat Novel Coronavirus and Influenza", bioRxlv, Mar. 14, 2020, pp. 1-20.

Fischbach et al., "Alizarin Red S for Online Pyrophosphate Detection Identified by a Rapid Screening Method", Scientific Reports, Mar. 24, 2017, pp. 1-9.

Patent Cooperation Treaty, International Search Report issued in PCT/US2021/029219, Oct. 27, 2021, pp. 1-6.

International Preliminary Report on Patentability (IPRP) dated Jan. 18, 2024, issued in related PCT/US2022/073538, filed on Jul. 8, 2022.

* cited by examiner

CRISPR-BASED PROGRAMMABLE RNA EDITING

CROSS-REFERENCE TO RELATED APPLICATIONS

This application claims the benefit of priority of U.S. Provisional Application No. 63/219,722, filed on Jul. 8, 2021, which is incorporated by reference herein for all purposes.

BACKGROUND

The emergence and spread of SARS-CoV-2 initiated a worldwide pandemic. The complete genome sequence of this novel coronavirus was determined and released the following year. Over a year later, the first genetic systems for SARS-CoV-2 were published and current methods for site specific manipulation of viral RNA involved a cumbersome multistep process that is time consuming and prone to error.

SUMMARY

The disclosure relates to programmable RNA editing using a type III CRISPR complex. For example, a type III CRISPR-Cas complex may be engineered to edit RNA. The type III CRISPR-Cas complex may be a type III-A Csm complex derived from *Streptococcus thermophilus* (SthCsm). The engineered CRISPR-Cas complex may be used to make sequence-specific modifications to RNA. The term "sequence-specific modification" may refer to changing RNA at a location that is targeted to a specific sequence of the RNA. The modifications may include a deletion in which a target portion is removed from the RNA, a replacement in which a target portion is removed and replaced with a synthetic RNA, base modifications and/or other changes to the RNA.

Type III CRISPR complexes rely on CRISPR RNA (crRNA)-guided nucleases that specifically cleave complementary RNA at six nucleotide intervals. To engineer a type III CRISPR complex, the RNA cleavage activity of a type III CRISPR complex is engineered to excise a sequence-specific region of target RNA or introduce a sequence-specific cut. For targeted deletion of the target portion of RNA, the RNA is repaired using splint ligation. Such repair may be in vitro. The result is an edited RNA with the target portion removed. For replacement of the target portion, the RNA a synthetic RNA complement is splinted prior ligation, resulting in the target portion being replaced with the synthetic RNA.

For testing and validation, examples herein will describe modifying a type III-A CRISPR RNA-guided nuclease for sequence-specific cleavage of the SARS-CoV-2 genome. The type III cleavage reaction is performed in vitro using purified viral RNA, resulting in sequence-specific cleavage at a single position or excision of 6, 12, 18 or 24 nucleotides. Ligation of the cleavage products is facilitated by a DNA splint that bridges the excision and RNA ligase is used to link the RNA products before transfection into mammalian cells. The SARS-CoV-2 RNA is infectious and standard plaque assays are used to recover viral clones. It should be noted, however, that a type III CRISPR-Cas complex may be engineered to make site-specific modifications to other RNA targets, whether genomic RNA or other types of RNA based on the disclosures herein. Collectively, the disclosures herein may be used for sequence-specific editing of RNA, which may be applicable for RNA viruses and gene therapy in general.

In some examples, the techniques described herein relate to a method of editing a ribonucleic acid (RNA) molecule, the method including: cleaving the RNA molecule with an engineered type III Clustered Regularly Interspaced Short Palindromic Repeat (CRISPR) complex to excise a target portion from the RNA molecule, the type III CRISPR complex including: a CRISPR RNA (crRNA) sequence that is programmed to be complementary to a target sequence of the RNA molecule; and a crRNA-guided nuclease that specifically cleaves the RNA molecule at the target portion when the engineered type III CRISPR complex is bound to the RNA molecule; and ligating cleaved ends of the RNA molecule that flank the excised target portion. Thus, the RNA molecule is programmatically edited based on the excised target portion and the ligated cleaved ends.

In some examples, the techniques described herein relate to a method, wherein ligating the cleaved ends of the RNA molecule includes inserting zero additional nucleotides between both ends and ligating together both ends of the RNA molecule to result in deletion of the target portion.

In some examples, the techniques described herein relate to a method, wherein ligating the cleaved ends of the RNA molecule includes inserting one or more additional modified or non-modified nucleotides between both ends and ligating together the one or more additional nucleotides and both ends of the RNA molecule to result in replacement of the target portion with the one or more additional nucleotides.

In some examples, the techniques described herein relate to a method, wherein ligating the cleaved ends of the RNA molecule includes using a nucleic acid splint that bridges both ends of the RNA molecule.

In some examples, the techniques described herein relate to a method, wherein the nucleic acid splint includes a deoxyribonucleic acid (DNA) splint.

In some examples, the techniques described herein relate to a method, wherein ligating the cleaved ends of the RNA molecule includes: inserting one or more additional nucleotides between both ends and ligating together the one or more additional nucleotides and both ends of the RNA molecule to result in replacement of the target portion with the one or more additional nucleotides, and wherein the nucleic acid splint includes a sequence that is complementary to a sequence of the one or more additional nucleotides.

In some examples, the techniques described herein relate to a method, wherein the engineered type III CRISPR complex includes a Csm complex.

In some examples, the techniques described herein relate to a method, wherein the crRNA-guided nuclease specifically cleaves the RNA molecule at intervals of one or more nucleotides.

In some examples, the techniques described herein relate to a method, wherein the intervals of one or more nucleotides includes intervals of six nucleotides.

In some examples, the techniques described herein relate to a method, wherein a number of the intervals is dependent on a length of the crRNA sequence.

In some examples, the techniques described herein relate to a method, wherein the length of the crRNA sequence is 40 nucleotides, the intervals of one or more nucleotides includes intervals of six nucleotides, and the number of the intervals is between three and four.

In some examples, the techniques described herein relate to a method, wherein the RNA molecule includes a viral genome, and the edited RNA molecule includes an edited virion.

In some examples, the techniques described herein relate to a method, wherein the virus includes the SARS-CoV-2 virus.

In some examples, the techniques described herein relate to a method, wherein the excising is performed in vitro, the method further including: recovering the edited virion; and transfecting the recovered edited virion into a host.

In some examples, the techniques described herein relate to a method, further including: how to engineer/program the type III CRISPR complex.

In some examples, the techniques described herein relate to a method of generating an engineered type III Clustered Regularly Interspaced Short Palindromic Repeat (CRISPR) complex to edit ribonucleic acid (RNA), including: generating a plurality of expression vectors including: (i) a CRISPR array having a natural or engineered CRISPR RNA (crRNA) transcript and a Cas subunit that processes pre-CRISPR transcripts into mature crRNA guide (i.e., Cas6 or Cas7-11), and (ii) a plurality of protein subunits of the type III CRISPR complex; co-transfecting the plurality of expression vectors into a host; inducing expression of the plurality of expression vectors in the host; and purifying the expressed plurality of expression vectors from the host.

In some examples, the techniques described herein relate to a method, further including: selecting purified products based on an expected size of the crRNA guide.

In some examples, the techniques described herein relate to a method, wherein the expected size is 46 nucleotides.

In some examples, the techniques described herein relate to a method, wherein the plurality of expression vectors includes: a first expression vector including the CRISPR array; a second expression vector including Cas10 and Csm2 subunits; and a third expression vector including Csm3, Csm4, and Csm5 subunits.

In some examples, the techniques described herein relate to a method, wherein the plurality of expression vectors includes: a first expression vector including the CRISPR array; a second expression vector including the gene for Cas7-11.

BRIEF DESCRIPTION OF THE FIGURES

Features of the present disclosure may be illustrated by way of example and not limited in the following figure(s), in which like numerals indicate like elements, in which.

DETAILED DESCRIPTION

Figure 1:
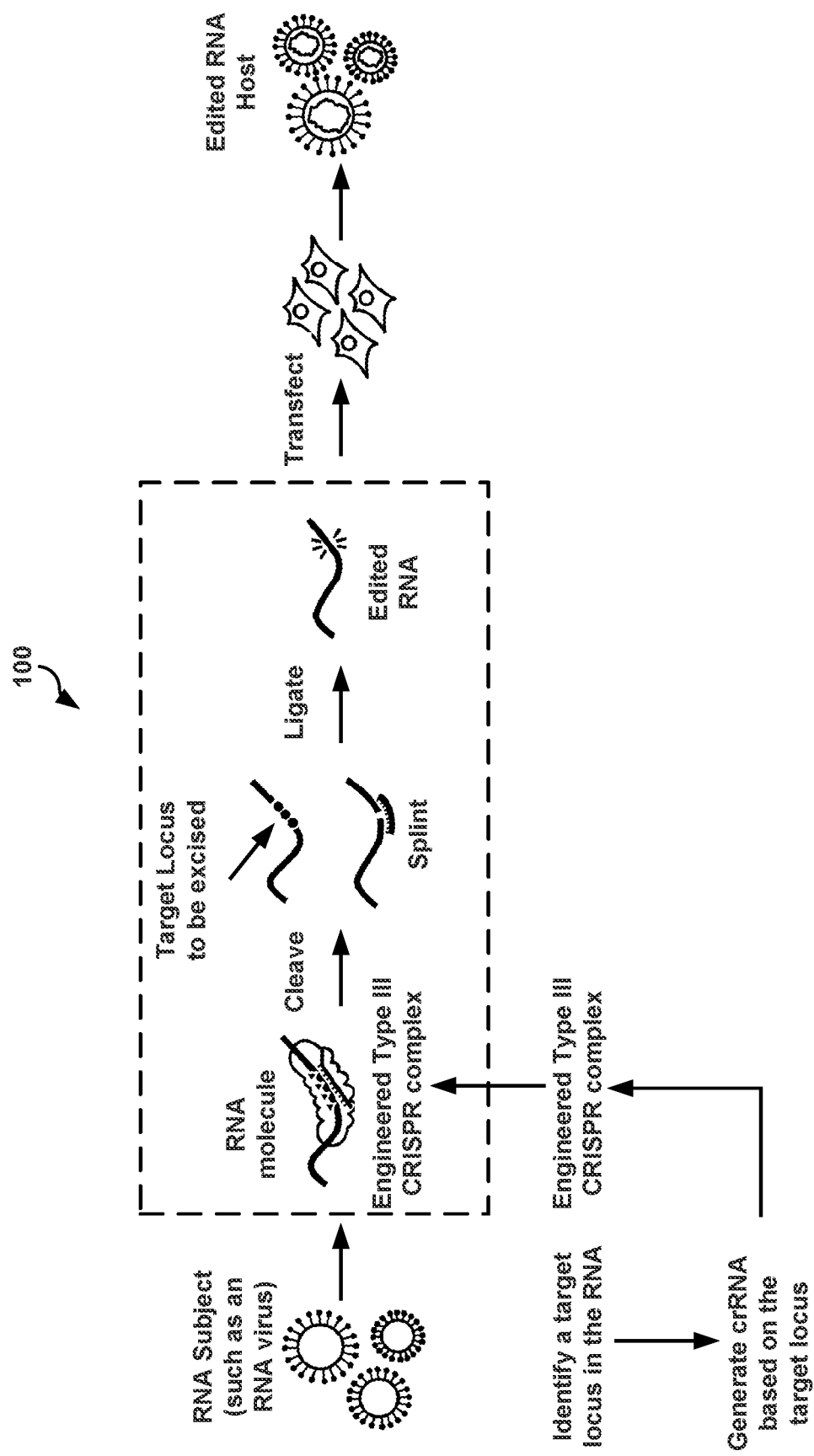
FIG. 1 illustrates a schematic overview of type III-based RNA editing, according to an implementation.

The disclosure relates to RNA editing using an engineered type III CRISPR complex. Many CRISPR RNA-guided nucleases are routinely used for sequence-specific manipulation of DNA. However, analogous methods for editing RNA have yet to be established. The use of CRISPR systems for editing RNA have been restricted to in vivo base editors that are incapable of deleting or inserting specific sequences by design. Thus, what is needed are RNA editing systems that enable specific RNA editing to address SARS-CoV-2 and other viral RNA pathogens, and more generally to programmatically edit any RNA for gene therapy or other purposes.

"RNA editing", "editing RNA", and similar terms may refer to deliberately modifying RNA. For example, RNA editing may include deleting a portion of the RNA that is intended to be removed, replacing the portion of the RNA with a synthetic RNA sequence that is intended to replace the portion of the RNA, adding synthetic RNA so that the edited RNA includes the synthetic RNA without replacement (even though some examples may remove RNA then add back the removed RNA), deleting one portion of RNA while adding a synthetic RNA, and/or otherwise modifying the RNA in an intentional manner. In some examples, RNA editing may be performed via a type III-E CRISPR Cas7-11 complex. RNA editing may be performed in vitro, in which case the edited RNA may be introduced into a host. RNA may include genomic RNA (such as viral genomic RNA) and/or other RNA molecules.

The term "engineered", and similar terms may refer to a deliberate generation of a system that is otherwise non-naturally occurring. Such engineering may include introducing one or more mutations to a genetic sequence, designing a genetic sequence, combining a set of components such as proteins and detection components where such combination does not occur in nature, and/or otherwise generating a non-naturally occurring system to edit nucleic acid such as RNA.

The engineered type III CRISPR complex may include a nuclease that cleaves RNA at specific sites guided by a CRISPR RNA (crRNA) sequence, which may be programmable. The term "programmatic", "programmable", and similar terms may refer to designing the engineered type III CRISPR complex to perform RNA editing. In particular, the programmable crRNA sequence refers to being designed to guide the engineered type III CRISPR complex to a specific target portion of interest in the RNA. For example, sequence specific targeting of crRNAs may be performed by designing synthetic spacer sequences. The synthetic spacer sequences may be between 20 and 60 nucleotides long that separate the repeat sequences or end with a self-cleaving ribozyme, such that the crRNA is processed into a short (20-100 nt) crRNA that is incorporated into an assembly of one or more Cas proteins, which together form a ribonucleoprotein complex that stably binds and cleaves RNAs that are complementary to the guide (spacer) sequence. The spacer sequences are designed to be complementary to a target sequence and intentionally designed to avoid complementarity to other "non-target" RNAs. In some examples, crRNA-guides are designed to include a protospacer flanking sequence (PFS) that facilitates binding, cleavage, or cyclic nucleotide synthesis. In other examples, the PFS is any sequence that is not complementary to the 5' repeat sequence of the crRNA. The programmable crRNA sequence may therefore facilitate specific cleavage of the RNA at one or more specific sites, enabling programmatic RNA editing. One example of an engineered type III CRISPR complex that may be used is a Csm complex, which is a type III-A CRISPR complex that has RNase activity. The Csm complex may be a SthCsm, derived from *S. thermophilus*.

Various examples described herein will refer to editing a viral RNA genome, such as the RNA genome of severe acute respiratory syndrome coronavirus 2 (SARS-CoV-2). However, any RNA molecule may be edited using the engineered type III CRISPR complex and methods disclosed herein.

FIG. 1 illustrates a schematic overview of RNA editing using an engineered type III CRISPR complex, according to an implementation. RNA to be edited may be referred to interchangeably as target RNA or an RNA molecule, although it will be understood that multiple RNA molecules are edited. To perform RNA editing, target RNA may be purified. For example, wild-type viral RNA may be purified from mammalian cell cultures infected by SARS-CoV-2.

The purified target RNA may be incubated with the engineered type III CRISPR complex. The programmable crRNA sequence may hybridize to the target RNA, binding the engineered type III CRISPR to the target RNA. The bound engineered type III CRISPR complex may cleave the RNA in vitro using a crRNA-guided nuclease that cleaves the target RNA at a target site guided by the crRNA sequence. At the target site, the crRNA-guided nuclease may cleave the target RNA at N-nucleotide increments. In particular, the crRNA-guided nuclease may cleave the target RNA at a single positon or in increments of 6 nucleotides. The number of increments may depend on the length of the crRNA and the composition or stoichiometry of Cas proteins in the complex. Typically, though not necessarily, the number of nucleases-active subunits may be three to four such that a total of 18 to 24 nucleotides are excised.

Following cleavage, the RNA fragments are treated to make the cleaved ends compatible with an RNA ligase for repair. For example, the RNA fragments may be treated with T4 PNK to make the cleaved ends biochemically compatible with T4 RNA ligase 1.

Figure 4A:
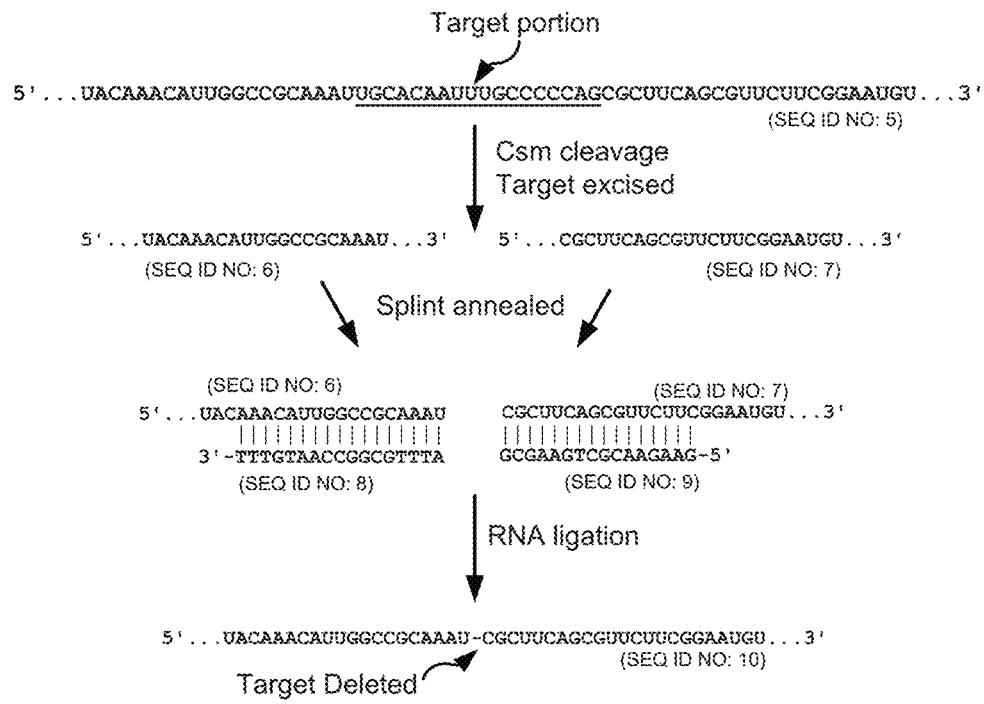
FIG. 4A illustrates programmable deletion of a target portion in RNA, according to an implementation.
Figure 4B:
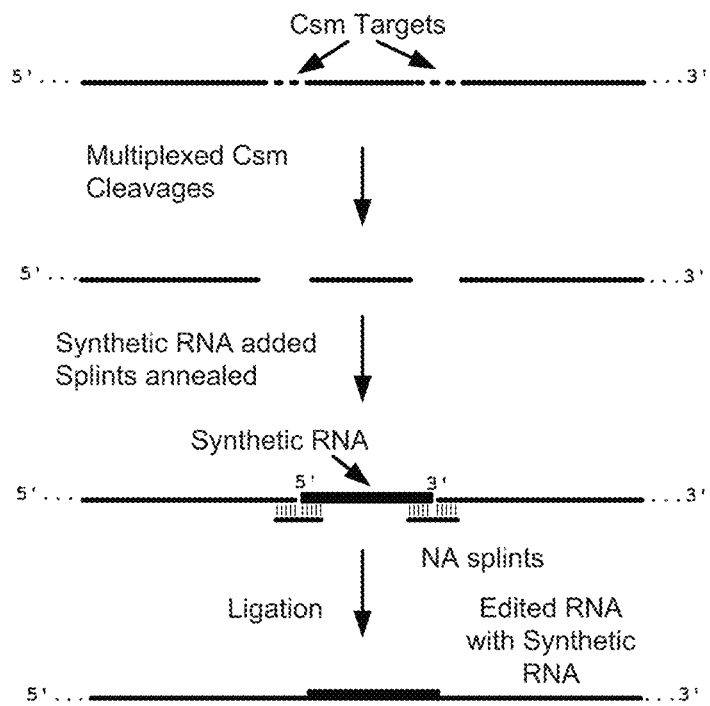
FIG. 4B illustrates programmable replacement of a target portion in RNA with a synthetic RNA molecule, according to an implementation.

The treated RNA fragments may be annealed to a nucleic acid oligonucleotide, which functions as a nucleic acid splint that bridges the two RNA fragments. The nucleic acid oligonucleotide may be an RNA oligonucleotide and/or a deoxyribonucleic acid (DNA) oligonucleotide. Thus, the nucleic acid splint may be an RNA splint and/or a DNA splint. The splinted structure (treated RNA fragments and annealed RNA splint and/or DNA splint) is then treated with a ligase that recognizes doubled stranded structures and repairs cleaved ends. For example, the ligase may be T4 RNA ligase 1, which recognizes the double stranded structure of the splinted structure and forms a phosphodiester bond between the cleaved genome fragments to thereby ligate the ends. It should be noted that such ligation may result in a deleted locus of interest (an example of which is illustrated in FIG. 4A) or in replacement of the locus with a synthetic sequence (an example of which is illustrated in (FIG. 4B). Following ligation, the edited RNA may be transfected into a host, such as mammalian cells. Edited virions be purified using standard plaque purification techniques.

In should be noted that in some type III systems (such as type III-A or type III-B), the nuclease is part of one subunit in the complex that assembles along the crRNA. Thus, the longer the crRNA, the more nuclease subunits and the larger number of cleavage events. Not all cleavage events occur at the same time so cleavage may be heterogeneous (i.e., some crRNA-guided complexes will cleave the target 4 times while others cleave twice). The nucleic acid splints are designed to enrich specific cleavage events by flanking specific sequences on either side of specific cleavage products. Some type III systems (type III-E) consist of a single polypeptide. These systems generally cleave the target at two positions that are separated by 6-nucleotides, but like other type III systems, the RNase active sites can be mutated, creating a cleavage defective complex that binds but does not cleave the target RNA or type III-E complexes can be engineered by mutating one of the two active sites so that they cleave the target RNA at one specific location.

Figure 2A:
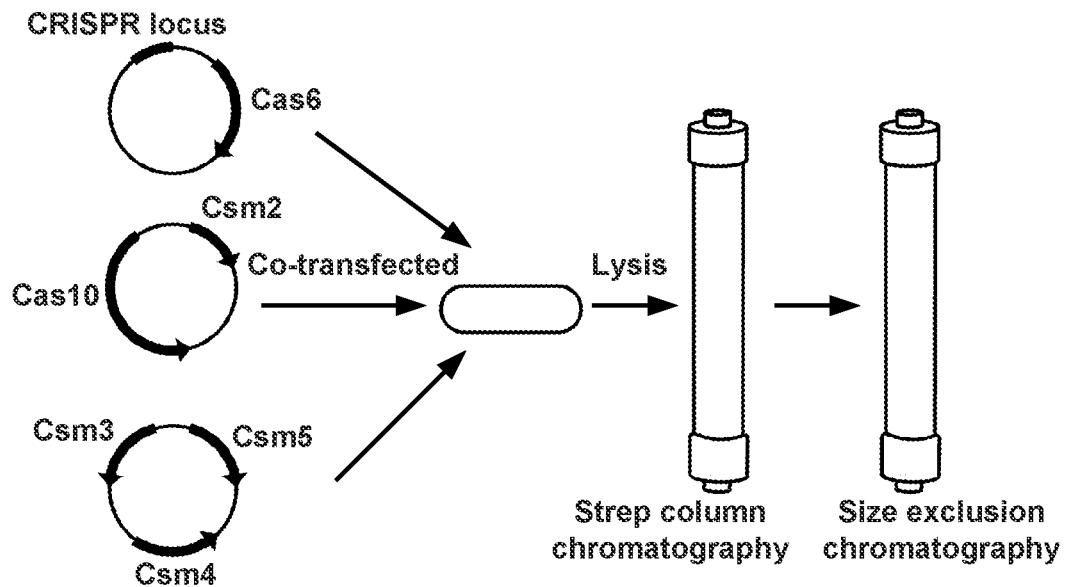
FIG. 2A illustrates an example of purifying a *Streptococcus thermophilus* Csm (SthCsm) complex, according to an implementation.

FIG. 2A illustrates an example of purifying an SthCsm complex, according to an implementation. SthCsm complex is expressed in *E. coli* by the co-transfection of three cloning vectors expressing the components of the Csm complex along with a CRISPR array that codes for a programmable guide and Cas6, which processes the crRNA transcript (having a specifically designed crRNA sequence) into a mature guide RNA (also referred to as a crRNA sequence). After induction of the expression vector, these cells are lysed, and the Csm complex is purified using standard methods including but not limited to running the lysate over an affinity column (i.e., strep column), followed by size exclusion chromatography.

To purify the type III-A Csm complex with guides designed to target SARS-CoV-2, a synthetic CRISPR was generated. The synthetic CRISPR includes four identical 36-nucleotide "spacers" that are flanked by the *Streptococcus thermophilus* CRISPR repeats. This CRISPR array is under the control of a T7 inducible promoter. Included in this cloning vector is the *S. thermophilus* gene for Cas6, which processes the crRNA transcript into a mature crRNA in some Type III CRISPR systems. The protein subunits of the Csm complex are sometimes split onto two expression vectors. Cas10 and Csm2 are on the pACYC-duet vector, while Csm3, Csm4, and Csm5 are on pRSF-1b vector. The Csm3 gene includes an N-terminus Strep-2 tag which is used for strep column chromatography. These three cloning vectors are co-transfected into *E. coli* BL21 (DE3) cells. The expression of these genes is under the control of a T7 promoter and is induced using Isopropyl β-d-1-thiogalactopyranoside (IPTG). After growth and induction of the expression vectors, Csm complexes were purified from these cells by strep column chromatography followed by size exclusion chromatography.

Figure 2B:
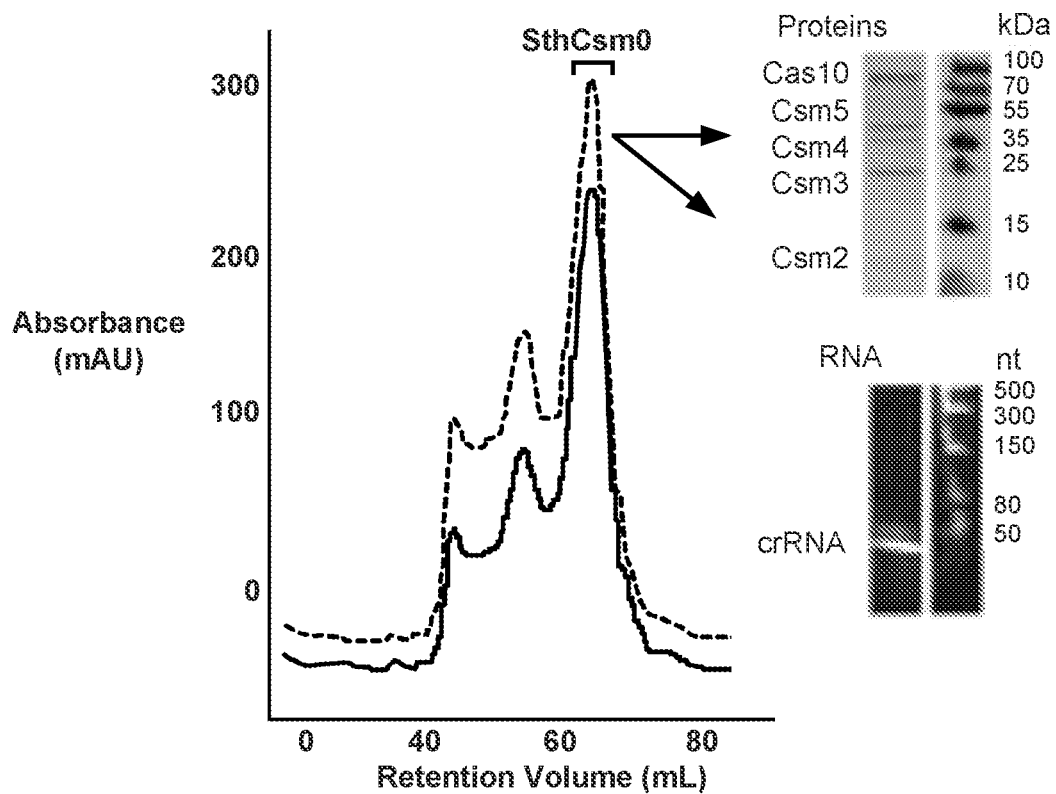
FIG. 2B illustrates an SEC profile of SthCsm, according to an implementation.

FIG. 2B illustrates an SEC profile of SthCsm, according to an implementation. The size exclusion chromatogram (SEC), SDS-PAGE of the purified proteins, and urea-PAGE of the associated crRNA, demonstrating the successful purification of the Csm complex, is shown in FIG. 2B. The SEC profile of SthCsm is shown here alongside SDS-PAGE of SthCsm complex and a denaturing urea acrylamide gel of nucleic acids associated with the SthCsm complex. Full-length crRNA guide is expected to be 40 nucleotides. However, other lengths (shorter or longer) are expected. For example, a mixture of crRNAs may be created as a population of crRNA species that vary in increments of 6 nucleotides. crRNA length is determined by efficiency of crRNA processing or by incorporating ribozymes into the 3'-end of the crRNA (e.g., HDV self-cleaving ribozyme). Natural processing of the crRNA in the cell is an inefficient process that results in a library of crRNAs that typically differ in 6 nucleotide increments that range from 28 to 72 nucleotides, although other ranges may be expected as well.

Figure 3A:
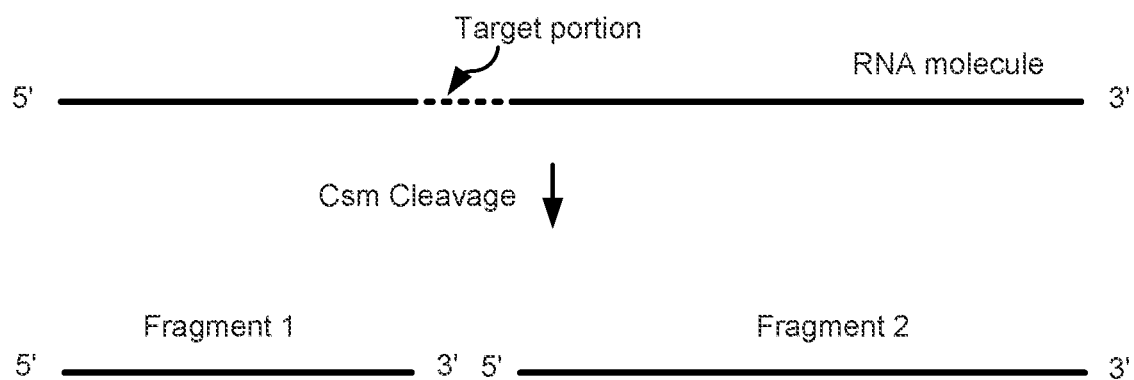
FIG. 3A illustrates programmable and specific cleavage by Csm of target portion in RNA, according to an implementation.

FIG. 3A illustrates programmable and specific cleavage by Csm of target portion in RNA, according to an implementation. Cleavage by Csm is programmable and specific. Here, an in vitro transcribed (IVT) 1.5 kb RNA molecule is cleaved by SthCsm programmed to recognize a target sequence within the IVT RNA.

RNA targeting by the engineered type III-A Csm complex (also referred to herein as "Csm complex") is strictly dependent on complementarity to the crRNA guide and does not rely on a protospacer adjacent motif (PAM), which simplifies guide design and eliminates constrains imposed by PAM distribution. Thus, the Csm complex can be directed to excise any 6, 12, 18 or 24 nucleotide sequence within an RNA genome. Other lengths of nucleotide sequences may be excised as well. The guide sequence is designed to have 36 nucleotides complementary to the target RNA. After transcription, the nascent crRNA transcript is processed by Cas6 and/or other nucleases to result mature crRNAs, the primary species being a 28 nucleotide crRNA composed of a 20 nucleotide guide and an 8 nucleotide 5' sequence derived from the repeat of the CRISPR. There is some heterogeneity in this processing, which results in a mix of differently sized mature crRNAs. The Csm complex assembles along the mature crRNA, as such, a smaller crRNA results in the assembly of a smaller complex. In this system, the most Csm complexes excise 12 to 24 nucleotides at the target region.

Cleavage of target RNA is performed by incubating the purified Csm complex with target RNA in vitro. SthCsm complex targeting the SARS-CoV-2 genome was incubated with purified viral genome in a 2:1 complex-to-genome molar ratio in a buffer composed of 20 mM HEPES (pH 7.5), 50 mM KCl, 0.1 mg/ml BSA, 10 mM Mg-acetate, and 1 U/uL murine RNAse inhibitor for 30 minutes at 37° C. This cleavage excises 6, 12, 18 or 24 nucleotides at the target sequence, dependent upon the crRNA associated with the Csm complex. Following cleavage, the genome fragments are purified using the Monarch RNA Cleanup Kit (NEB).

Figure 3B:
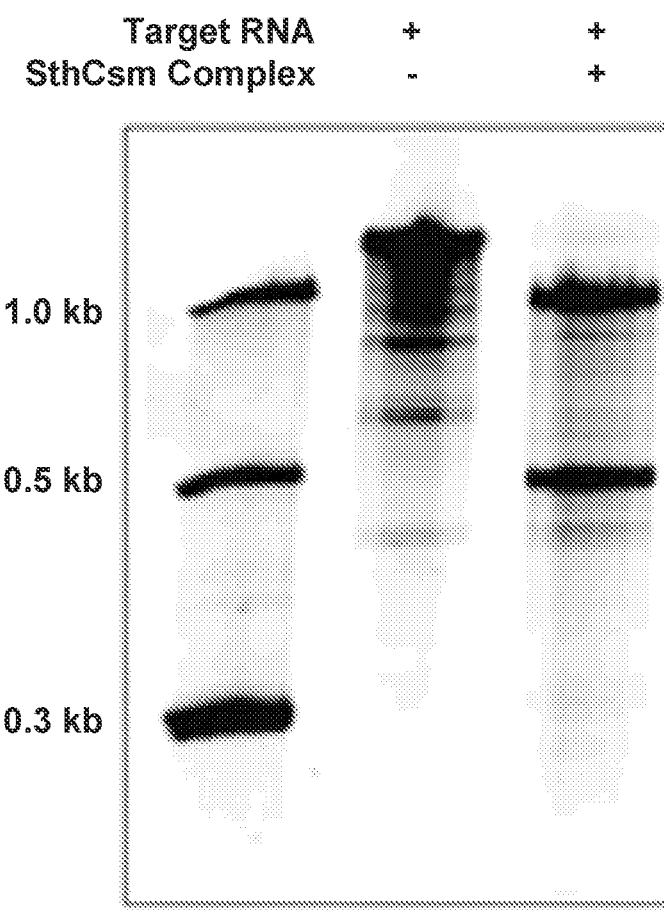
FIG. 3B illustrates an example of urea-PAGE showing discreet products of programmable cleavage by Csm, according to an implementation.

FIG. 3B illustrates an example of urea-PAGE showing discreet products of programmable cleavage by Csm, according to an implementation. This cleavage results in discreet products sized 1.0 kb and 0.5 kb, demonstrated by urea-PAGE. This programmable cleavage is the basis for RNA editing.

FIG. 4A illustrates programmable deletion of a target portion in RNA, according to an implementation. To delete a target region of a target RNA (such as an RNA genome), Csm cleavage is performed followed by splint ligation. A splint is designed to have 15-25 nucleotides of complementarity to the end of each cleavage product to be ligated. After PNK treatment, the cleaved target RNA fragments are mixed with the splint in a 1:1 target RNA-to-splint ratio. The splint is then annealed to the available from target RNA fragments by briefly heating the mixture to 95° C. in a thermocycler then ramping the temperature down to 4° C. over 45 minutes. This RNA:DNA complex is then treated with RNA ligase 1 (available from New England Biolabs®) to result in an edited target RNA with the target deletion.

Following cleavage with Csm, the genome fragments are treated with T4 PNK (available from New England Biolabs®). Csm is a metal dependent nuclease that leave 2'-3' cyclic phosphate on the 3' cleavage product and hydroxyl on the 5' end. The 2'-3' cyclic phosphate is replaced with 2' and 3' hydroxyls by treating the cleaved genome fragments with T4 PNK in 1X PNK buffer at 37° C. for 40 minutes. The reaction is then supplemented with ATP to 1 mM and incubated at 37° C. for an additional 40 minutes to replace the 5' hydroxyl group with a 5' monophosphate group. Following PNK treatment, the genome fragments are purified using the MONARCH RNA Cleanup Kit (available from New England Biolabs®).

Splint ligation first involves the annealing of the RNA fragments to a DNA oligonucleotide that bridges the cleaved region by base pairing to the two cleavage products. This splinted RNA-DNA hybrid is treated with T4 RNA ligase 1, which connected the two-cleavage product with a phosphodiester bond.

The DNA oligonucleotide splint is mixed with PNK-treated genome fragments in a 1:1 splint-to-genome molar ratio in 1× T4 RNA ligase buffer. To anneal the fragments to the splint, the mixture is heated to 95° C. for 2 minutes, then slowly ramped down to 4° C. over 45 minutes in a thermocycler. Following annealing of the splint to the cleaved genome fragments, the RNA:DNA hybrid is treated with T4 RNA ligase 1 (available from New England Biolabs®) following manufacturer protocol in 1× ligase buffer supplemented with 10% PEG 8000 and 1 U/ul murine RNAse inhibitor. The reaction is incubated at 25° C. for 1 hour. The reaction is then treated with 1 uL TURBO DNase (ThermoFisher Scientific) and incubated for 15 minutes at 37° C. to remove the DNA splint. RNA is then purified using the MONARCH RNA Cleanup Kit (available from New England Biolabs®). This results in an edited RNA genome with the target RNA removed.

This cleavage and splint ligation approach to RNA editing may also be applied further to replace a region of a viral RNA genome with a synthetic RNA sequence of interest. To accomplish this, Csm complexes with multiplexed guides (i.e. two Csm complexes with guides recognizing two sites in the genome) are used to cleave the RNA genome at two sites flanking the region to be replaced. The resulting cleavage products are then treated with T4 PNK, as described above, and mixed with a synthetic RNA molecule. Two DNA splints that were designed to hybridize with the genome fragments and the synthetic RNA are then annealed to the RNA molecules. This structure is then treated with T4 RNA ligase 1 which seals the nicks between the genome fragments and the synthetic RNA, resulting in directed integration of synthetic RNA into a viral genome. This approach to RNA editing is outlined in FIG. 4B.

FIG. 4B illustrates programmable replacement of a target portion in target RNA (such as an RNA genome) with a synthetic RNA molecule, according to an implementation. To replace a region of the target RNA with a synthetic RNA molecule, one or more Csm complexes are used to cleave the target RNA. The cleavage products are PNK treated, and the synthetic RNA of interest is added to the cleavage products in a 1:1 target RNA-to-synthetic RNA ratio. Two splints designed to hybridize with the cleaved target RNA ends and synthetic RNA are then added to the mix and annealed to the genome and synthetic RNA as above. This RNA:DNA complex is then treated with RNA ligase 1 (available from New England Biolabs®) which results in integration of the synthetic RNA into the RNA target.

Figure 5A:
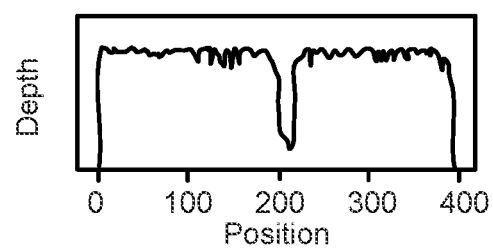
FIG. 5A illustrates validation of target portion deletion based on sequencing, according to an implementation.
Figure 5A:
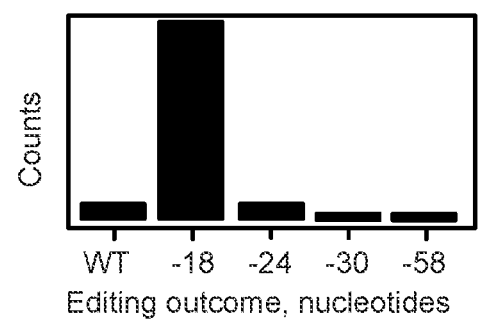
Figure 5B:
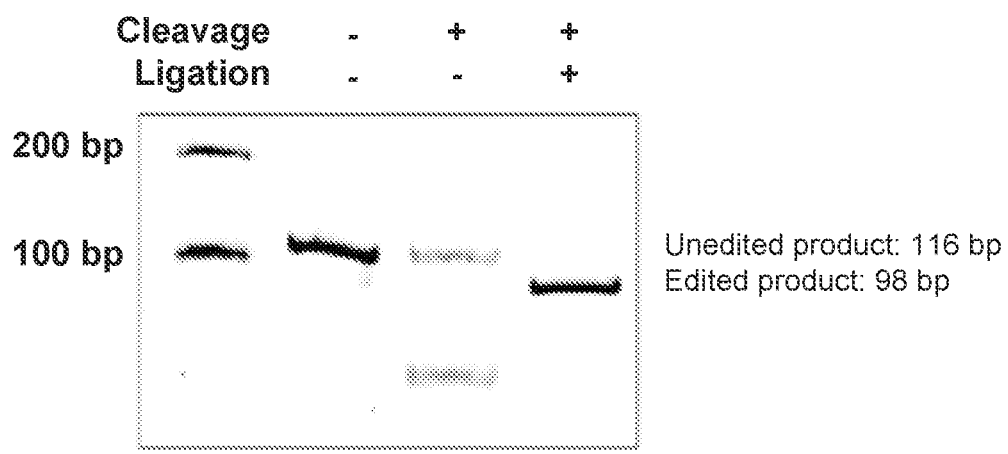
FIG. 5B illustrates validation of target portion deletion based on PCR amplification products, according to an implementation.

FIG. 5A illustrates validation of target portion deletion based on sequencing, according to an implementation. Following cleavage by SthCsm and splint ligation, the RNA was reverse transcribed, PCR amplified, and sequenced by Oxford Nanopore sequencing. A. Sequencing results demonstrate a drop in sequence depth at the target site. This is indicative of the desired 18-nucleotide deletion.

To validate this approach, we created a synthetic CRISPR for the type III A Csm complex from Streptococcus thermophilus that is designed to target the ORF7a gene of SARS-CoV-2. Cleavage efficiency is measured by RT-qPCR using primer pairs that flank the cleavage site. Using this approach, we routinely cleave >98% of the target RNA. Following cleavage, the products are reconnected using splint ligation. The efficiency of ligation is measured using the same RT-qPCR assay. We routinely achieve ligation efficiencies of ~25%. To verify that the approach results in the expected deletion, we deep sequenced across the edited region of the RNA. The sequencing data reveals that the primary product is an RNA containing the desired 18-nucleotide deletion, FIG. 5A. This is further confirmed by the formation of a smaller RT-PCR product following editing, demonstrated in FIG. 5B.

FIG. 5B illustrates validation of target portion deletion based on PCR amplification products, according to an implementation. PCR amplification across edited region reveals a decrease in size of the edited product. This shift in size is expected, as the editing excises 18 nucleotides Another possible iteration of this RNA editing procedure depends on host RNA ligases encoded by mammalian cells. Specifically, RNA editing may be mediated by the mammalian tRNA ligase complex. This suggests that Csm-mediated RNA editing might be possible in vivo, and that mammalian tRNA ligase complex could eliminate the dependence on PNK treatment, splint annealing, and in vitro ligation steps.

Collectively, these results demonstrate that RNA editing by Csm, followed by splint ligation is an effective procedure that results in the expected edited product. Csm cleavage is programmable and completely PAM independent, as such, we expect this RNA editing technology to be generalizable to any RNA molecule, with a major application being facile editing of RNA viruses. This approach is unique, as no other methods have been reported which accomplish editing of RNA via programmable cleavage and ligation of an RNA molecule in vitro. We anticipate that nuclease defective type III complexes could also serves as platforms that target base editors, and other RNA modifying enzymes to specific RNA sequences by design, which would enable genetic and epigenetic editing without cleavage.

The crRNA sequence may be a CRISPR guide sequence that is engineered to be complementary to a locus of the nucleic acid, such as the RNA target. The crRNA sequence may be selected based on one or more conserved regions of the target nucleic acid or other region of interest. For example, different genomes of the SARS-CoV-2 virus (or other RNA target) may be aligned with one another to identify conserved regions. Generally speaking, regions having a greater alignment (fewer base pair differences and longer alignment lengths) than regions having lesser alignment are better candidates for generating a complementary sequence to use as the CRISPR guide sequence.

The crRNA sequence may be designed based on conserved regions across different samples of the SARS-CoV-2, different strains of the SARS-CoV-2, and/or other samples available for the SARS-CoV-2. Such conserved sequence may be determined based on sequence alignments. A pairwise match may be considered when an alignment quality of the pairwise match is sufficient to determine that aligned portions of two sequences represent a conservation of the nucleotides in the sequences across genomes of SARS-CoV-2 (or other target). The alignment quality may be specified as having a minimum overlap of at least about 1 base, 2 bases, 4 bases, 4 bases, 5 bases, 10 bases, 15 bases, 40 bases, 25 bases, 40 bases, 45 bases, 40 bases, 45 bases, 50 bases, 55 bases, 60 bases, 65 bases, 70 bases, 75 bases, 80 bases, 85 bases, 90 bases, 95 bases, or 100 bases. Alternatively, or additionally, the alignment quality may be based on a minimum alignment identity of at least about 5%, 10%, 15%, 40%, 25%, 40%, 45%, 40%, 45%, 50%, 55%, 60%, 65%, 70%, 75%, 80%, 85%, 90%, 95%, or more. In some cases, a criterion may require at least a 25-nt overlap with at least about 70% identity.

In this example, the sequencing encoding the SARS-CoV-2 nucleocapsid (N) and ORF7a genes were selected to serve as the basis for generating the CRISPR guide sequence. Examples of the CRISPR guide sequence include SEQ ID NO. 1-SEQ ID NO. 4.

Sequences

A sequence listing, named "065869-0570004_SEQUENCE_LISTING.xml", created Jul. 18, 2023, 10,065 bytes, in XML format accompanies this application. The sequence listing is incorporated by reference in its entirety herein for all purposes.

TABLE 1

Examples of sequences.

| SEQ ID NO. | Sequence | Description |
|---|---|---|
| 1 | ACGGAAACAAGCGCUGGGGGCAAA UUGUGCAAUUUGCGGCCAAU | A crRNA guide targeting Csm-complex from *Streptococcus thermophilus* to edit N-gene of SARS-CoV-2 |
| 2 | ACGGAAACACUACCAAGAGUGUGU UAGAGGUACAACAGUACUUU | A crRNA guide targeting Csm-complex from *Streptococcus thermophilus* to edit ORF7a-gene of SARS-CoV-2 |
| 3 | UUGAUGUCACGGAACAAGCGCUGG GGGCAAAUUGUGCAAUUUGCGGCC AAU | A crRNA guide targeting Csm-complex (Cas7-11) from *Desulfonema ishimotonii* to edit N-gene of SARS-CoV-2 |

TABLE 1-continued Examples of sequences.

| SEQ ID NO. | Sequence | Description |
|---|---|---|
| 4 | UUGAUGUCACGGAACACUACCAAGAGUGUGUUAGAGGUACAACAGUACUUU | A crRNA guide targeting Csm-complex (Cas7-11) from *Desulfonema ishimotonii* to edit ORF7a -gene of SARS-CoV-2 |

Figure 6A:
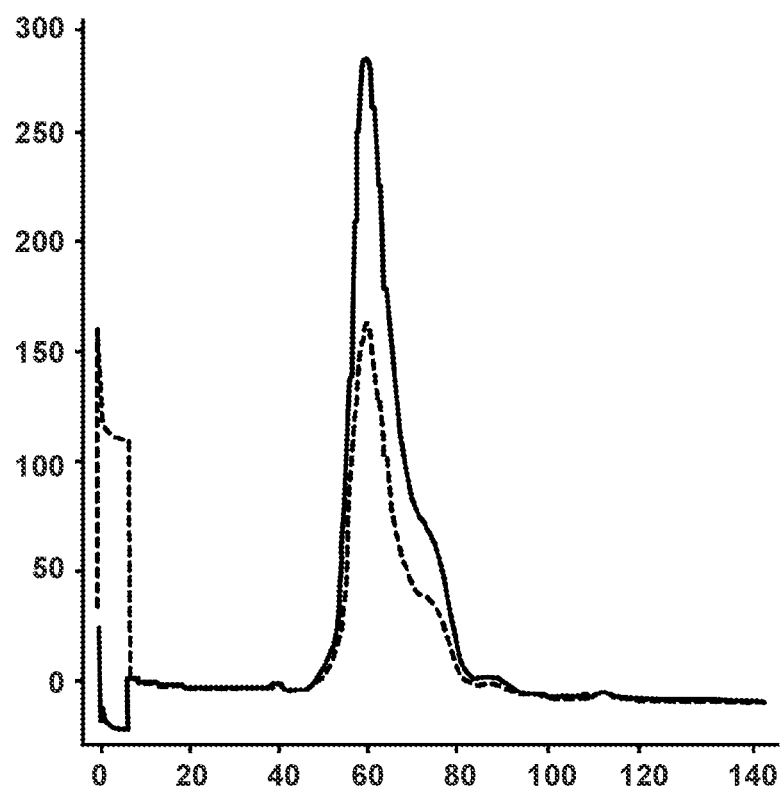
FIG. 6A illustrates an SEC profile of the *Desulfonema ishimotonii* Cas7-11 protein purified from *E. coli*, according to an implementation.

FIG. 6A illustrates an SEC profile of the *Desulfonema ishimotonii* Cas7-11 (DisCas7-11) protein purified from *E. coli*, according to an implementation. DisCas7-11 complex is expressed in *E. coli* by the co-transfection of one cloning vector expressing single polypeptide. After induction of the expression vector, these cells are lysed, and the Type III-E complex polyprotein is purified using standard methods including but not limited to running the lysate over an affinity column (i.e., strep column), followed by size exclusion chromatography.

After purification the complex is mixed with 1.2× concentration of pre-mature crRNA (66 nt) that includes full sequence of the direct repeat (35 nt) from CRISPR locus and 31 nt spacer sequence that is reverse complementary to the target sequence. Cas7-11 polyprotein is then incubated with pre-mature crRNA in a buffer composed of 20 mM HEPES (pH 7.5), 50 mM KCl, 0.1 mg/ml BSA, 10 mM Mg-acetate, and 1 U/uL murine RNAse inhibitor for 30 minutes at 37° C. This reaction promotes complexing of Cas7-11 protein with the crRNA and crRNA processing that involves trimming the direct repeat sequence leaving a 15 nt 5'-tag.

Figure 6B:
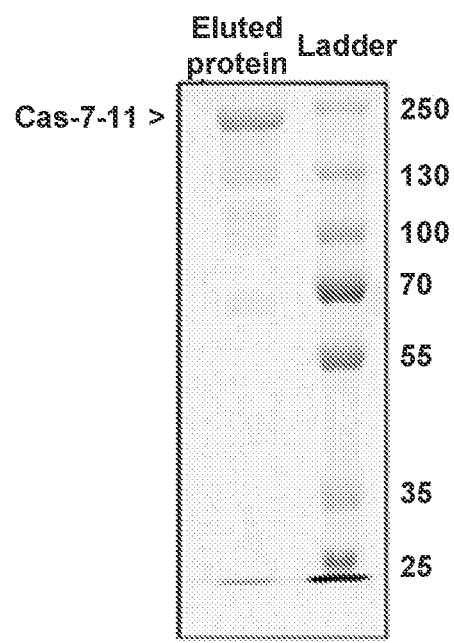
FIG. 6B illustrates an SDS-PAGE of the SEC purified *Desulfonema ishimotonii* Cas7-11 protein purified from *E. coli*, according to an implementation.

FIG. 6B illustrates an SDS-PAGE of the SEC purified *Desulfonema ishimotonii* Cas7-11 protein purified from *E. coli*, according to an implementation.

Figure 6C:
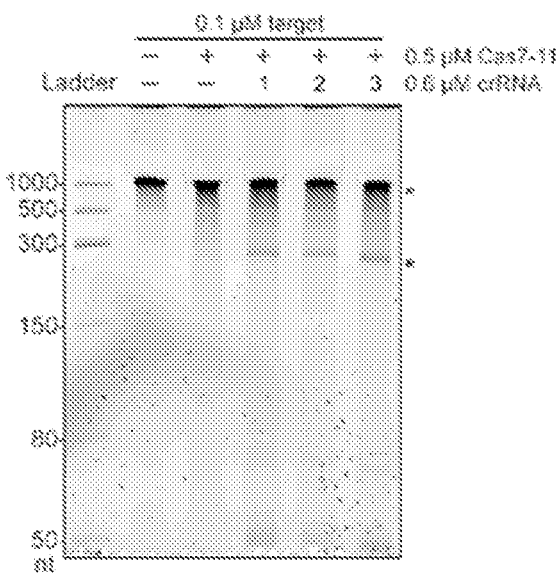
FIG. 6C illustrates a urea-PAGE of sequence-specific target RNA cleavage by purified *Desulfonema ishimotonii* Cas7-11 protein, according to an implementation.

FIG. 6C illustrates a urea-PAGE of sequence-specific target RNA cleavage by purified *Desulfonema ishimotonii* Cas7-11 protein, according to an implementation. This cleavage results in discreet products sized 0.9 kb and 0.25 kb, demonstrated by urea-PAGE. Cleavage of target RNA is performed by incubating the purified DisCas7-11 complex with target RNA in vitro. DisCas7-11 complex targeting sequence of the GFP gene was incubated with synthetic in vitro transcribed RNA fragment of the recombinant Sindbis-GFP virus (SINV-GFP) in a 5:1 complex-to-genome molar ratio in a buffer composed of 20 mM HEPES (pH 7.5), 50 mM KCl, 0.1 mg/ml BSA, 10 mM Mg-acetate, and 1 U/uL murine RNAse inhibitor for 60 minutes at 37° C. This cleavage excises 6 nucleotides at the target sequence, dependent upon the crRNA associated with the Csm complex. Following cleavage, the RNA fragments were purified from proteins with phenol-chloroform extraction method and resolved using Urea-PAGE.

Figure 6D:
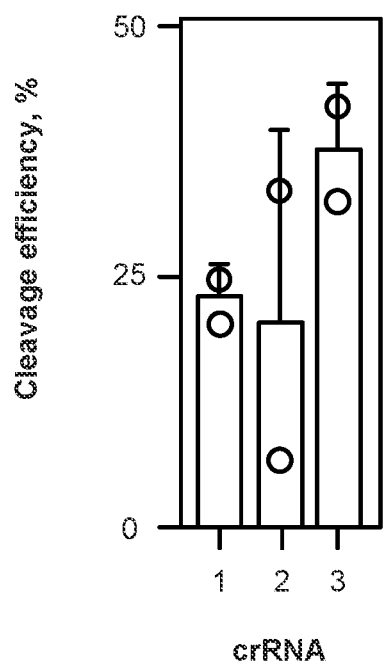
FIG. 6D illustrates a quantification of sequence-specific target RNA cleavage by purified *Desulfonema ishimotonii* Cas7-11 protein, according to an implementation.

FIG. 6D illustrates a quantification of sequence-specific target RNA cleavage by purified *Desulfonema ishimotonii* Cas7-11 protein, according to an implementation. RNA cleavage products were reverse transcribed with LunaScript RT SuperMix Kit (New England Biolabs) and quantified using real-time PCR with primers flanking the cleavage site. Data was normalized to a control reaction without crRNA and cleavage efficiency was calculated as (1−relative quantity of RNA)*100%. Reactions were performed in technical duplicates and data was plotted as mean±one standard deviation.

Target RNA may be obtained from a subject. For example, the target RNA may be an RNA of an organism that infects a host organism. In particular, the target RNA may be an RNA genome of a virus that has infected the subject. In another example, the target RNA may be the RNA of the subject. A subject may refer to an animal, such as a mammalian species (preferably human) or avian (e.g., bird) species, or other organism, such as a plant. More specifically, a subject can be a vertebrate, e.g., a mammal such as a mouse, a primate, a simian or a human. Animals include farm animals, sport animals, and pets. A subject can be a healthy individual, an individual that has symptoms or signs or is suspected of having a disease or a predisposition to the disease, or an individual that is in need of therapy or suspected of needing therapy.

A genetic modification or mutation in the context of an engineered system may refer to an alteration, variant or polymorphism in a nucleic acid that may result in altered or disabled functionality of a corresponding protein. Such alteration, variant or polymorphism can be with respect to a reference genome, the subject or other individual. Variations include one or more single nucleotide variations (SNVs), insertions, deletions, repeats, small insertions, small deletions, small repeats, structural variant junctions, variable length tandem repeats, and/or flanking sequences, CNVs, transversions, gene fusions and other rearrangements may also be considered forms of genetic variation. A variation can be a base change, insertion, deletion, repeat, copy number variation, transversion, or a combination thereof.

A "polynucleotide", "nucleic acid", "nucleic acid molecule", or "oligonucleotide" may each refer to a polymer of nucleosides (including deoxyribonucleosides, ribonucleosides, or analogs thereof) joined by inter-nucleosidic linkages. Typically, a polynucleotide comprises at least three nucleosides. Oligonucleotides often range in size from a few monomeric units, e.g. 3-4, to hundreds of monomeric units. Whenever a polynucleotide is represented by a sequence of letters, such as "AUGCCUG," it will be understood that the nucleotides are in 5' to 3' order from left to right and that "A" denotes adenosine, "C" denotes cytidine, "G" denotes guanosine, and "U" denotes uracil, unless otherwise noted. The letters A, C, G, and U (or "T" denoting thymine in DNA) may be used to refer to the bases themselves, to nucleosides, or to nucleotides comprising the bases, as is standard in the art.

All patent filings, websites, other publications, sequence listings, accession numbers and the like cited above or below are incorporated by reference in their entirety for all purposes to the same extent as if each individual item were specifically and individually indicated to be so incorporated by reference.

If different versions of a sequence are associated with an accession number at different times, the version associated with the accession number at the effective filing date of this application is meant. The effective filing date means the earlier of the actual filing date or filing date of a priority application referring to the accession number if applicable.

Likewise, if different versions of a publication, website or the like are published at different times, the version most recently published at the effective filing date of the application is meant unless otherwise indicated. Any feature, step, element, embodiment, or aspect of the disclosure can be used in combination with any other unless specifically indicated otherwise. Although the present disclosure has been described in some detail by way of illustration and example for purposes of clarity and understanding, it will be apparent that certain changes and modifications may be practiced within the scope of the appended claims.

What is claimed is:

1. A method of editing a ribonucleic acid (RNA) molecule, the method comprising:
cleaving the RNA molecule with a non-naturally occurring type III Clustered Regularly Interspaced Short Palindromic Repeat (CRISPR) complex to excise a target portion from the RNA molecule, the non-naturally occurring type III CRISPR complex comprising:
a CRISPR RNA (crRNA) sequence that is designed to be complementary to a target sequence of the RNA molecule; and
a crRNA-guided nuclease that specifically cleaves the RNA molecule at the target portion when the non-naturally occurring type III CRISPR complex is bound to the RNA molecule; and
ligating cleaved ends of the RNA molecule that flank the excised target portion, wherein the RNA molecule is programmatically edited based on the excised target portion and the ligated cleaved ends.

2. The method of claim 1, wherein ligating the cleaved ends of the RNA molecule comprises inserting zero additional nucleotides between both ends and ligating together both ends of the RNA molecule to result in deletion of the target portion.

3. The method of claim 1, wherein ligating the cleaved ends of the RNA molecule comprises inserting one or more additional nucleotides between both ends and ligating together the one or more additional nucleotides and both ends of the RNA molecule to result in replacement of the target portion with the one or more additional nucleotides.

4. The method of claim 1, wherein ligating the cleaved ends of the RNA molecule comprises using a nucleic acid splint that bridges both ends of the RNA molecule.

5. The method of claim 4, wherein the nucleic acid splint is a deoxyribonucleic acid (DNA) splint.

6. The method of claim 4, wherein ligating the cleaved ends of the RNA molecule comprises:
inserting one or more additional nucleotides between both ends and ligating together the one or more additional nucleotides and both ends of the RNA molecule to result in replacement of the target portion with the one or more additional nucleotides, and
wherein the nucleic acid splint includes a sequence that is complementary to a sequence of the one or more additional nucleotides.

7. The method of claim 1, wherein the non-naturally occurring type III CRISPR complex is a Csm complex.

8. The method of claim 1, wherein the crRNA-guided nuclease specifically cleaves the RNA molecule at intervals of one or more nucleotides.

9. The method of claim 8, wherein the intervals of one or more nucleotides comprises intervals of six nucleotides.

10. The method of claim 8, wherein a number of the intervals is dependent on a length of the crRNA sequence.

11. The method of claim 10, wherein the length of the crRNA sequence is 36 nucleotides, the intervals of one or more nucleotides comprises intervals of six nucleotides, and the number of the intervals is between three and four.

12. The method of claim 1, wherein the RNA molecule is a virus and the edited RNA molecule is an edited virion.

13. The method of claim 12, wherein the virus is the SARS-COV-2 virus.

14. The method of claim 12, wherein the excising is performed in vitro, the method further comprising:
recovering the edited virion; and
transfecting the recovered edited virion into a host.

15. A method of editing a ribonucleic acid (RNA) molecule, comprising:
cleaving the RNA molecule with a non-naturally occurring type III Clustered Regularly Interspaced Short Palindromic Repeat (CRISPR) complex to excise a target portion from the RNA molecule, the non-naturally occurring type III CRISPR complex comprising:
a CRISPR RNA (crRNA) sequence that is designed to be complementary to a target sequence of the RNA molecule; and
a crRNA-guided nuclease that specifically cleaves the RNA molecule at the target portion at intervals of six nucleotides when the non-naturally occurring type III CRISPR complex is bound to the RNA molecule; and
ligating cleaved ends of the RNA molecule that flank the excised target portion, wherein the RNA molecule is programmatically edited based on the excised target portion and the ligated cleaved ends.

* * * * *

```
                         SEQUENCE LISTING

Sequence total quantity: 10
SEQ ID NO: 1           moltype = RNA  length = 44
FEATURE                Location/Qualifiers
source                 1..44
                       mol_type = other RNA
                       organism = synthetic construct
SEQUENCE: 1
acggaaacaa gcgctggggg caaattgtgc aatttgcggc caat                   44

SEQ ID NO: 2           moltype = RNA  length = 44
FEATURE                Location/Qualifiers
source                 1..44
                       mol_type = other RNA
                       organism = synthetic construct
SEQUENCE: 2
acggaaacac taccaagagt gtgttagagg tacaacagta cttt                   44

SEQ ID NO: 3           moltype = RNA  length = 51
FEATURE                Location/Qualifiers
source                 1..51
                       mol_type = other RNA
                       organism = synthetic construct
SEQUENCE: 3
ttgatgtcac ggaacaagcg ctgggggcaa attgtgcaat ttgcggccaa t            51

SEQ ID NO: 4           moltype = RNA  length = 51
FEATURE                Location/Qualifiers
source                 1..51
                       mol_type = other RNA
                       organism = synthetic construct
SEQUENCE: 4
ttgatgtcac ggaacactac caagagtgtg ttagaggtac aacagtactt t            51

SEQ ID NO: 5           moltype = RNA  length = 61
FEATURE                Location/Qualifiers
source                 1..61
                       mol_type = other RNA
                       organism = synthetic construct
SEQUENCE: 5
tacaaacatt ggccgcaaat tgcacaattt gcccccagcg cttcagcgtt cttcggaatg  60
t                                                                  61

SEQ ID NO: 6           moltype = RNA  length = 20
FEATURE                Location/Qualifiers
source                 1..20
                       mol_type = other RNA
                       organism = synthetic construct
SEQUENCE: 6
tacaaacatt ggccgcaaat                                              20

SEQ ID NO: 7           moltype = RNA  length = 23
FEATURE                Location/Qualifiers
source                 1..23
                       mol_type = other RNA
                       organism = synthetic construct
SEQUENCE: 7
cgcttcagcg ttcttcggaa tgt                                          23

SEQ ID NO: 8           moltype = DNA  length = 17
FEATURE                Location/Qualifiers
source                 1..17
                       mol_type = other DNA
                       organism = synthetic construct
SEQUENCE: 8
tttgtaaccg gcgttta                                                 17
```

```
SEQ ID NO: 9           moltype = DNA  length = 16
FEATURE                Location/Qualifiers
source                 1..16
                       mol_type = other DNA
                       organism = synthetic construct
SEQUENCE: 9
gcgaagtcgc aagaag                                                         16

SEQ ID NO: 10          moltype = RNA  length = 43
FEATURE                Location/Qualifiers
source                 1..43
                       mol_type = other RNA
                       organism = synthetic construct
SEQUENCE: 10
tacaaacatt ggccgcaaat cgcttcagcg ttcttcggaa tgt                           43
```